US008882796B2

(12) United States Patent
Martinez

(10) Patent No.: US 8,882,796 B2
(45) Date of Patent: *Nov. 11, 2014

(54) THREE ELEMENT COAXIAL VASO-OCCLUSIVE DEVICE

(75) Inventor: George Martinez, Brea, CA (US)

(73) Assignee: MicroVention, Inc., Tustin, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/594,707

(22) Filed: Aug. 24, 2012

(65) Prior Publication Data

US 2012/0323268 A1 Dec. 20, 2012

Related U.S. Application Data

(63) Continuation of application No. 10/631,981, filed on Jul. 31, 2003, now Pat. No. 8,273,100.

(60) Provisional application No. 60/400,013, filed on Jul. 31, 2002.

(51) Int. Cl.
A61M 29/00 (2006.01)
A61B 17/12 (2006.01)
A61B 17/00 (2006.01)

(52) U.S. Cl.
CPC ..... A61B 17/12022 (2013.01); A61B 17/12113 (2013.01); A61B 2017/00867 (2013.01); A61B 2017/00004 (2013.01); A61B 2017/1205 (2013.01); A61B 17/12177 (2013.01); A61B 17/12145 (2013.01); A61B 17/1215 (2013.01); A61B 2017/0084 (2013.01); A61B 17/1219 (2013.01)
USPC .......................................................... 606/200

(58) Field of Classification Search
CPC .............. A61M 25/104; A61M 25/10; A61M 25/1002; A61M 29/02; A61M 25/1011; A61M 2025/1052; A61M 25/0032; A61M 2025/1013; A61F 2/958; A61F 2/95; A61F 2002/011; A61B 17/12022; A61B 2017/1205; A61B 17/12136; A61B 17/12109; A61B 2017/00557; A61B 17/12113; A61B 17/12145; A61B 17/1214

USPC ......... 606/108, 151, 159, 191, 192, 193, 194, 606/195, 196, 197, 198, 199, 200, 213; 623/1.11, 1.12, 1.23

See application file for complete search history.

(56) References Cited

U.S. PATENT DOCUMENTS 3,709,842 A 1/1973 Stoy et al.
3,749,085 A 7/1973 Willson et al.
(Continued)

FOREIGN PATENT DOCUMENTS

WO WO97/26939 A1 7/1997
WO WO97/27888 A1 8/1997
(Continued)

OTHER PUBLICATIONS

United States Patent and Trademark Office, Notice of Allowance mailed May 25, 2012 in U.S. Appl. No. 10/631,981, 5 pages.
(Continued)

Primary Examiner — Jonathan W Miles
(74) Attorney, Agent, or Firm — Inskeep IP Group, Inc.

(57) ABSTRACT

A vaso-occlusive device includes inner, intermediate, and outer elements arranged coaxially. The inner element is a filamentous element, preferably a microcoil. The intermediate element is made of a non-metallic material, preferably an expansile polymer. The outer element is substantially non-expansile and defines at least one gap or opening through which the intermediate element is exposed. In a preferred embodiment, when the intermediate element is expanded, it protrudes through the at least one gap or opening in the outer element and assumes a configuration with an undulating, convexly-curved outer surface defining a chain of arcuate segments, each having a diameter significantly greater than the diameter of the outer element. The expanded configuration of the intermediate element minimizes friction when the device is deployed through a microcatheter, thereby reducing the likelihood of buckling while maintaining excellent flexibility. The result is a device with enhanced pushability and trackability when deployed through a microcatheter.

22 Claims, 3 Drawing Sheets

(56) References Cited

U.S. PATENT DOCUMENTS

| | | | |
|---|---|---|---|
| 4,020,829 A | 5/1977 | Willson et al. | |
| 4,301,803 A | 11/1981 | Handa et al. | |
| 4,304,232 A | 12/1981 | Michaels | |
| 4,365,621 A | 12/1982 | Brundin | |
| 4,402,319 A | 9/1983 | Handa et al. | |
| 4,493,329 A | 1/1985 | Crawford et al. | |
| 4,509,504 A | 4/1985 | Brundin | |
| 4,529,739 A | 7/1985 | Scott et al. | |
| 4,551,132 A | 11/1985 | Pásztor et al. | |
| 4,614,188 A * | 9/1986 | Bazell et al. | 606/194 |
| 4,663,358 A | 5/1987 | Hyon et al. | |
| 4,795,741 A | 1/1989 | Leshchiner et al. | |
| 4,819,637 A | 4/1989 | Dormandy, Jr. et al. | |
| 4,932,419 A | 6/1990 | de Toledo | |
| 4,951,677 A | 8/1990 | Crowley et al. | |
| 4,994,069 A | 2/1991 | Ritchart et al. | |
| 5,120,349 A | 6/1992 | Stewart et al. | |
| 5,127,484 A | 7/1992 | Bares et al. | |
| 5,129,180 A | 7/1992 | Stewart | |
| 5,133,731 A | 7/1992 | Butler et al. | |
| 5,154,705 A | 10/1992 | Fleischhacker et al. | |
| 5,163,952 A | 11/1992 | Froix | |
| 5,165,421 A | 11/1992 | Fleischhacker et al. | |
| 5,226,911 A | 7/1993 | Chee et al. | |
| 5,258,042 A | 11/1993 | Mehta | |
| 5,295,959 A * | 3/1994 | Gurbel et al. | 604/103.13 |
| 5,304,194 A | 4/1994 | Chee et al. | |
| 5,312,415 A | 5/1994 | Palemo | |
| 5,350,397 A | 9/1994 | Palermo et al. | |
| 5,354,290 A | 10/1994 | Gross | |
| 5,373,619 A | 12/1994 | Fleischhacker et al. | |
| 5,382,259 A | 1/1995 | Phelps et al. | |
| 5,382,260 A | 1/1995 | Dormandy, Jr. et al. | |
| 5,443,478 A | 8/1995 | Purdy | |
| 5,449,369 A | 9/1995 | Imran | |
| 5,456,693 A | 10/1995 | Conston et al. | |
| 5,469,867 A | 11/1995 | Schmitt | |
| 5,476,472 A | 12/1995 | Dormandy, Jr. et al. | |
| 5,483,022 A | 1/1996 | Mar | |
| 5,509,899 A * | 4/1996 | Fan et al. | 604/103.14 |
| 5,522,822 A | 6/1996 | Phelps et al. | |
| 5,525,334 A | 6/1996 | Ito et al. | |
| 5,536,274 A | 7/1996 | Neuss | |
| 5,541,234 A | 7/1996 | Unger et al. | |
| 5,573,520 A | 11/1996 | Schwartz et al. | |
| 5,573,994 A | 11/1996 | Kabra et al. | |
| 5,578,074 A | 11/1996 | Mirigian | |
| 5,580,568 A | 12/1996 | Greff et al. | |
| 5,582,610 A | 12/1996 | Grossi et al. | |
| 5,582,619 A | 12/1996 | Ken | |
| 5,609,629 A | 3/1997 | Fearnot et al. | |
| 5,612,050 A | 3/1997 | Rowe et al. | |
| 5,624,461 A | 4/1997 | Mariant | |
| 5,624,685 A | 4/1997 | Takahashi et al. | |
| 5,634,936 A | 6/1997 | Linden et al. | |
| 5,645,558 A | 7/1997 | Horton | |
| 5,658,308 A | 8/1997 | Snyder | |
| 5,672,634 A | 9/1997 | Tseng et al. | |
| 5,678,296 A | 10/1997 | Fleischhacker et al. | |
| 5,690,666 A | 11/1997 | Berenstein et al. | |
| 5,690,667 A | 11/1997 | Gia | |
| 5,690,671 A | 11/1997 | McGurk et al. | |
| 5,718,711 A | 2/1998 | Berenstein et al. | |
| 5,725,568 A | 3/1998 | Hastings | |
| 5,749,894 A | 5/1998 | Engelson | |
| 5,750,585 A | 5/1998 | Park et al. | |
| 5,752,974 A | 5/1998 | Rhee et al. | |
| 5,766,160 A | 6/1998 | Samson et al. | |
| 5,823,198 A | 10/1998 | Jones et al. | |
| 5,853,418 A | 12/1998 | Ken et al. | |
| 5,883,705 A | 3/1999 | Minne et al. | |
| 5,891,155 A | 4/1999 | Irie | |
| 5,976,162 A | 11/1999 | Doan et al. | |
| 5,980,514 A | 11/1999 | Kupiecki et al. | |
| 6,004,338 A | 12/1999 | Ken et al. | |
| 6,013,084 A | 1/2000 | Ken et al. | |
| 6,015,424 A | 1/2000 | Rosenbluth et al. | |
| 6,066,149 A | 5/2000 | Samson et al. | |
| 6,093,199 A | 7/2000 | Brown et al. | |
| 6,096,034 A | 8/2000 | Kupiecki et al. | |
| 6,136,015 A | 10/2000 | Kurz et al. | |
| 6,159,165 A | 12/2000 | Ferrera et al. | |
| 6,159,239 A * | 12/2000 | Greenhalgh | 623/1.13 |
| 6,168,570 B1 | 1/2001 | Ferrera | |
| 6,171,326 B1 | 1/2001 | Ferrera et al. | |
| 6,179,857 B1 | 1/2001 | Diaz et al. | |
| 6,193,728 B1 | 2/2001 | Ken et al. | |
| 6,231,590 B1 | 5/2001 | Slaikeu et al. | |
| 6,238,403 B1 | 5/2001 | Greene, Jr. et al. | |
| 6,245,090 B1 | 6/2001 | Gilson et al. | |
| 6,280,457 B1 | 8/2001 | Wallace et al. | |
| 6,287,318 B1 | 9/2001 | Villar et al. | |
| 6,299,604 B1 | 10/2001 | Ragheb et al. | |
| 6,299,619 B1 | 10/2001 | Greene, Jr. et al. | |
| 6,299,627 B1 | 10/2001 | Eder et al. | |
| 6,312,421 B1 | 11/2001 | Boock | |
| 6,399,886 B1 | 6/2002 | Avellanet | |
| 6,423,085 B1 | 7/2002 | Murayama et al. | |
| 6,517,570 B1 * | 2/2003 | Lau et al. | 623/1.13 |
| 6,623,450 B1 | 9/2003 | Dutta | |
| 6,634,361 B1 | 10/2003 | Nikolchev et al. | |
| 6,723,108 B1 | 4/2004 | Jones et al. | |
| 6,849,081 B2 | 2/2005 | Sepetka et al. | |
| 7,066,904 B2 | 6/2006 | Rosenthal et al. | |
| 8,273,100 B2 * | 9/2012 | Martinez | 606/200 |
| 2001/0023325 A1 | 9/2001 | Ferrera | |
| 2001/0046518 A1 | 11/2001 | Sawhney | |
| 2002/0020417 A1 | 2/2002 | Nikolchev et al. | |
| 2002/0040239 A1 | 4/2002 | Murayama et al. | |
| 2002/0151910 A1* | 10/2002 | Gellman et al. | 606/139 |
| 2002/0169473 A1 | 11/2002 | Sepetka et al. | |
| 2005/0171572 A1 | 8/2005 | Martinez | |
| 2007/0299464 A1 | 12/2007 | Cruise et al. | |
| 2008/0208167 A1 | 8/2008 | Stankus et al. | |
| 2009/0232869 A1 | 9/2009 | Greene, Jr. et al. | |
| 2011/0245863 A1* | 10/2011 | Martinez | 606/200 |

FOREIGN PATENT DOCUMENTS

| | | |
|---|---|---|
| WO | WO98/01421 A1 | 1/1998 |
| WO | WO99/23954 A1 | 5/1999 |
| WO | WO99/44538 A1 | 9/1999 |
| WO | WO99/56783 A1 | 11/1999 |
| WO | WO99/65401 A1 | 12/1999 |
| WO | WO00/27445 A1 | 5/2000 |
| WO | WO00/74577 A1 | 12/2000 |
| WO | WO02/05731 A1 | 1/2002 |

OTHER PUBLICATIONS

United States Patent and Trademark Office, Examiner's Answer to Appeal Brief mailed Jan. 15, 2010 in U.S. Appl. No. 10/631,981, 10 pages.

United States Patent and Trademark Office, Final Office Action mailed Mar. 10, 2009 in U.S. Appl. No. 10/631,981, 15 pages.

United States Patent and Trademark Office, Final Office Action mailed Nov. 7, 2008 in U.S. Appl. No. 10/631,981, 8 pages.

United States Patent and Trademark Office, Office Action mailed Mar. 14, 2008 in U.S. Appl. No. 10/631,981, 9 pages.

United States Patent and Trademark Office, Office Action mailed May 7, 2007 in U.S. Appl. No. 10/631,981, 9 pages.

United States Patent and Trademark Office, Office Action mailed Sep. 21, 2006 in U.S. Appl. No. 10/631,981, 15 pages.

Murayama, Y. et al., "Cellular Responses of Bioabsorbable Polymeric Material and Guglielmi Detachable Coil in Experimental Aneurysms," *Stroke*, Apr. 2002, Nov. 20, 1128, 9 pages.

Ahuja, a.A. et al., "Platinum Coil Coatings to Increase Thrombogenicity: A Preliminary Study in Rabbits," *American Journal of Neuroradiology*, 14:794-798, Jul./Aug. 1993, 6 pages.

Zollikofer, C. et al., "A Combination of Stainless Steel Coil and Compressed Ivalon: A New Technique for Embolization of Large Arteries and Arteriovenous Fistulas," *Radiology*, Jan. 1981, 138(1):229-31, 6 pages.

(56) References Cited

OTHER PUBLICATIONS

WIPO, U.S. International Search Authority, International Search Report and Written Opinion mailed Dec. 17, 2010 in International Patent Application No. PCT/US2010/053972, 8 pages.
Persidis, A., "Tissue engineering," *Nature Biotechnology* 17, 508-510 (May 1999), abstract, 1 page.
Hoekstra, D., "Hyaluronan-Modified Surfaces for Medical Devices," *Medical Device & Diagnostic Industry* Feb. 1999, pp. 48-56, 6 pages.
Graves, V. B. et al., "Endovascular Occlusion of the Carotid or Vertebral Artery with Temporary Proximal Flow Arrest and Microcoils: Clinical Results," AJNR Am J Neuroradial (Aug. 1997) vol. 18, pp. 1201-1206.
Schmutz, F. et al., "Embolization of cerebral arteriovenous malformations with silk: histopathologic changes and hemorrhagic complications," *AJNR Am J Neuroradiol* (Aug. 1997) vol. 18, pp. 1233-1237, 5 pages.
Graves, V.B. et al., "Endovascular Occlusion of the Carotid or Vertebral Artery with Temporary Proximal Flow Arrest and Microcoils: Clinical Results," *AJNR Am J Nueroradiol* (Aug. 1997) vol. 18, pp. 1201-1206, 6 pages.
Viñuela, F. et al., "Guglielmi detachable coil embolization of acute intracranial aneurysm; perioperative anatomical and clinical outcome in 403 patients," *J Neurosurg* (Mar. 1997) vol. 86, pp. 475-482, 8 pages.

Horák, D. et al., "New radiopaque polyHEMA-based hydrogel particles," *J Biomed Mater Res* Feb. 1997;34(2):183-8, 6 pages.
Hogg, P.J. et al., "Interaction of platelet-derived growth factor with thrombospondin 1," *Biochem. J.* (1997) 326, 709-716, 8 pages.
Woerly, S. et al., "Intracerebral Implantation of Hydrogel-Coupled Adhesion Peptides: Tissue Reaction," *Journal of Neural Transplantation & Plasticity* vol. 5, No. 4, 1995, pp. 245,255, 11 pages.
Chirila, T.V. et al., "Poly(2-hydroxyethyl metharcrylate) sponges ans implant materials: in vivo and in vitro evaluation of cellular invasion," *Biomaterials* 1993;14(1):26-38, 13 pages.
Edelman, E.R. et al., "Controlled and modulated release of basic fibroblast growth factor," *Biomaterials* Sep. 1991, vol. 12, pp. 619-626, 8 pages.
Larsen, N. E. et al., "Hylan gel composition for percutaneous embolization," *Journal of Biomedical Materials Research* vol. 25, Issue 6, 699-710 (Jun. 1991), 12 pages.
Horak, D. et al., "Hydrogels in endovascular embolization. II. Clinical use of spherical particles," *Biomaterials*, Nov. 1986; 7(6):467-470, 4 pages.
Zollikofer, C. et al., "Therapeutic Blockade of Arteries Using Compressed Ivalon," *Radiology* 136:635-640, Sep. 1980, 6 pages.
Latchaw, R.E. et al., "Polyvinyl foam embolization of vascular and neoplastic lesions of the nead, neck, and spine," *Radiology* Jun. 1979, 131:669-679, 11 pages.

\* cited by examiner

THREE ELEMENT COAXIAL VASO-OCCLUSIVE DEVICE

CROSS-REFERENCE TO RELATED APPLICATION

This application is a continuation of U.S. patent application Ser. No. 10/631,981 filed Jul. 31, 2003 now U.S. Pat. No. 8,273,100 entitled Three Element Coaxial Vaso-Occlusive Device, which claims the benefit, under 35 U.S.C. Section 119(e), of U.S. Provisional Application Ser. No. 60/400,013, filed Jul. 31, 2002 entitled Three Layer Coaxial Vaso-Occlusive Device, both of which are incorporated herein by reference in their entireties.

FEDERALLY-SPONSORED RESEARCH OR DEVELOPMENT

Not Applicable

BACKGROUND

This invention relates to vaso-occlusive devices, such as vaso-occlusive coils and the like, for the embolization of vascular aneurysms and similar vascular abnormalities. Specifically, the invention is an improvement over existing two layer or two element coaxial vaso-occlusive devices, particularly those having a polymer coating or covering. In particular, the present invention is a three layer or three element coaxial vaso-occlusive device that provides improved durability, pushability, and trackability inside a microcatheter. The characteristic termed "trackability" relates to the ease of advancing one interventional device within or over another, and it is related to friction and flexibility.

Vaso-occlusive devices are typically used within the vasculature of the human body to block the flow of blood through a vessel through the formation of an embolus. Vaso-occlusive devices are also used to form an embolus within an aneurysm stemming from the vessel. Vaso-occlusive devices can be formed of one or more elements, generally delivered into the vasculature via a catheter or similar mechanism.

The embolization of blood vessels is desired in a number of clinical situations. For example, vascular embolization has been used to control vascular bleeding, to occlude the blood supply to tumors, and to occlude vascular aneurysms, particularly intracranial aneurysms. In recent years, vascular embolization for the treatment of aneurysms has received much attention. Several different treatment modalities have been employed in the prior art. One approach that has shown promise is the use of thrombogenic microcoils. These microcoils may be made of a biocompatible metal alloy (typically platinum and tungsten) or a suitable polymer. If made of metal, the coil may be provided with Dacron fibers to increase thrombogenicity. The coil is deployed through a microcatheter to the vascular site. Examples of microcoils are disclosed in the following U.S. Pat. No. 4,994,069—Ritchart et al.; U.S. Pat. No. 5,133,731—Butler et al.; U.S. Pat. No. 5,226,911—Chee et al.; U.S. Pat. No. 5,312,415—Palermo; U.S. Pat. No. 5,382,259—Phelps et al.; U.S. Pat. No. 5,382,260—Dormandy, Jr. et al.; U.S. Pat. No. 5,476,472—Dormandy, Jr. et al.; U.S. Pat. No. 5,578,074—Mirigian; U.S. Pat. No. 5,582,619—Ken; U.S. Pat. No. 5,624,461—Mariant; U.S. Pat. No. 5,645,558—Horton; U.S. Pat. No. 5,658,308—Snyder; and U.S. Pat. No. 5,718,711—Berenstein et al.

A specific type of microcoil that has achieved a measure of success is the Guglielmi Detachable Coil ("GDC"), described in U.S. Pat. No. 5,122,136—Guglielmi et al. The GDC employs a platinum wire coil fixed to a stainless steel delivery wire by a solder connection. After the coil is placed inside an aneurysm, an electrical current is applied to the delivery wire, which electrolytically disintegrates the solder junction, thereby detaching the coil from the delivery wire. The application of the current also creates a positive electrical charge on the coil, which attracts negatively-charged blood cells, platelets, and fibrinogen, thereby increasing the thrombogenicity of the coil. Several coils of different diameters and lengths can be packed into an aneurysm until the aneurysm is completely filled. The coils thus create and hold a thrombus within the aneurysm, inhibiting its displacement and its fragmentation.

The advantages of the GDC procedure are the ability to withdraw and relocate the coil if it migrates from its desired location, and the enhanced ability to promote the formation of a stable thrombus within the aneurysm.

A more recent development in the field of microcoil vaso-occlusive devices is exemplified in U.S. Pat. No. 6,299,619—Greene, Jr. et al. and U.S. Pat. No. 6,602,261—Greene, Jr. et al., both assigned to the assignee of the subject invention. These patents disclose vaso-occlusive devices comprising a microcoil with one or more expansile elements disposed on the outer surface of the coil. The expansile elements may be formed of any of a number of expansile polymeric hydrogels, or alternatively, environmentally-sensitive polymers that expand in response to a change in an environmental parameter (e.g., temperature or pH) when exposed to a physiological environment, such as the blood stream.

While the microcoils with expansile elements have exhibit great promise in, for example, embolizing aneurysms of a wide variety of sizes and configurations, the expansile elements increase the frictional forces between the vaso-occlusive device and a microcatheter through which the device is deployed. Furthermore, depending on the configuration and material of the expansile elements, the flexibility of the device may be reduced. These factors may result in a device that has less than optimal pushability (resistance to buckling) and reduced trackability (as defined above).

There has thus been a long-felt, but as yet unsatisfied need for a microcoil vaso-occlusive device that has all the advantages of the expansile element type of device, and that also exhibits enhanced pushability and trackability, with good durability characteristics.

SUMMARY OF THE INVENTION

Broadly, the present invention is a vaso-occlusive device, comprising three coaxial elements: an elongate, flexible, filamentous inner element; a non-metallic intermediate element coaxially surrounding the inner element and in intimate contact therewith; and an outer element coaxially surrounding the intermediate element and in intimate contact therewith, the outer element including one or more openings or gaps through which the intermediate element is exposed.

In a preferred embodiment of the invention, the inner element is in the form of a helical coil made of a biocompatible, radiopaque metal, and the intermediate element is a conformal coating or layer on the inner element, the conformal coating or layer being made of a soft polymeric material that is preferably an expansile polymer. Advantageously, the polymeric hydrogel is an environmentally-responsive hydrogel that expands upon exposure to the physiological environment, for example, of the blood stream. The polymer may advantageously be bio-absorbable or biodegradable. Also in the preferred embodiment, the outer element is a helical "over-coil" that is loosely wound ("open-wound") over the intermediate element, except at proximal and distal end sections, where it is tightly wound ("close-wound"). The close-wound proximal and distal end sections support the inner element, protecting it from damage during deployment and any necessary repositioning, while also securely binding the intermediate element to the inner element at the proximal and distal ends of the device and restraining the hydrogel of the intermediate element from expanding at the respective ends of the device. The open-wound section between the proximal and distal end sections creates a single, continuous helical opening through which the intermediate element expands. The helical configuration of the opening forces the expanded polymeric intermediate element to assume the configuration of a chain of arcuate segments protruding radially outwardly between the coils of the over-coil, rather than that of a continuous polymeric layer having a continuous, uninterrupted exterior surface. Because each of the arcuate segments contacts the interior surface of a microcatheter (e.g., during deployment) primarily at or near a tangential contact point, the total contact area of the intermediate element is reduced as compared to a continuous axial polymeric element. This reduced contact area correspondingly reduces the aggregate friction between the polymeric layer and the microcatheter, thereby decreasing the resistance to manipulation of the device. The open-wound section also creates hinge points between the arcuate segments of the polymeric intermediate element, thereby increasing the overall flexibility of the device.

It has been confirmed experimentally that the reduced friction and increased flexibility afforded by the outer element, and by the interaction between the outer and intermediate elements, enhances the both the pushability and trackability of a device made in accordance with the present invention, as compared, for example, with prior art microcoil devices having expansile polymeric coatings or elements on or along their exterior surfaces.

The invention thus provides a microcoil vaso-occlusive device with an expansile element that allows the device to embolize very efficiently a wide variety of vascular abnormalities, e.g., aneurysms of a wide variety of shapes, sizes, and locations, and yet that exhibits enhanced pushability and trackability as compared to the prior art.

DESCRIPTION OF THE INVENTION

Figure 1:
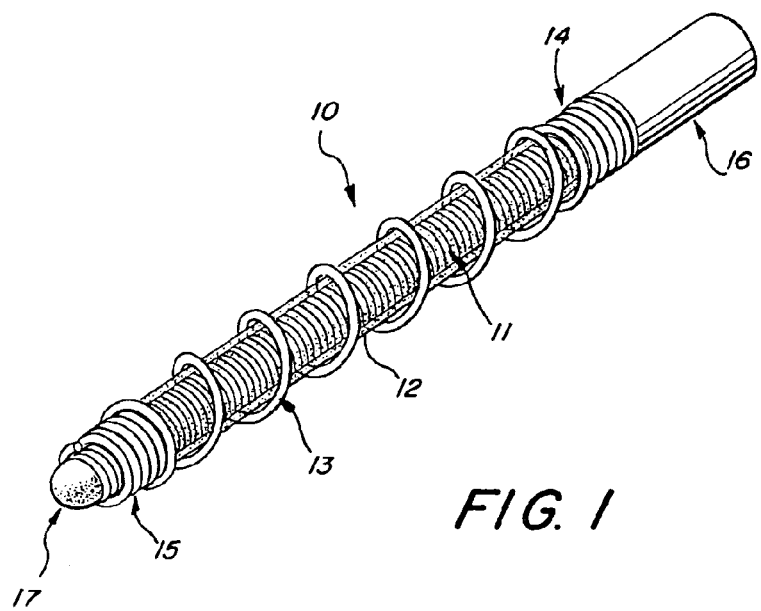
FIG. 1 is a perspective view of a vaso-occlusive device in accordance with a preferred embodiment of the present invention.
Figure 2:
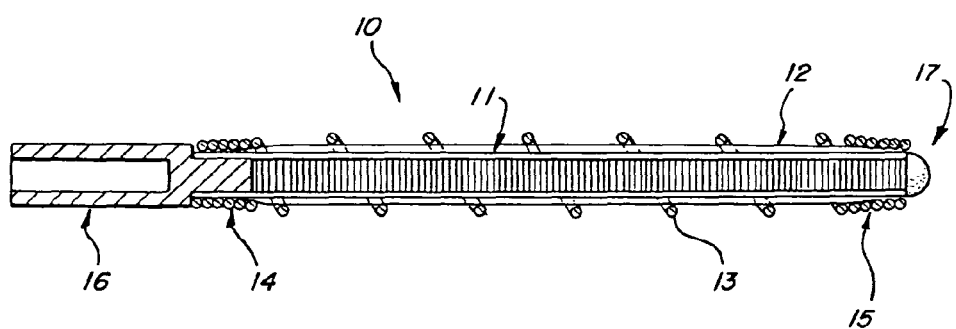
FIG. 2 is an axial cross-sectional view of the device of FIG. 1.

Referring to FIGS. 1-4, a vaso-occlusive device 10, in accordance with a preferred embodiment of the invention, comprises three elongate, coaxial elements: an inner core element 11, a non-metallic intermediate element 12, and a non-expansile outer element 13 that covers at least a portion of the intermediate element. The intermediate element 12 is in intimate contact with both the inner element 11 and the outer element 13.

The inner element 11 is formed of a flexible, elongate filament or wire that is preferably made of a material that allows visualization under various medical imaging means, such as X-ray, MRI, or ultrasound. Preferably, the inner element 11 is formed from a length of wire made of any of various biocompatible, radiopaque metals, such as platinum, tantalum, tungsten, gold, titanium, nitinol, stainless steel, Elgiloy (cobalt-chromium-nickel), or other suitable alloys known in the art. Alternatively, it can be made from or include non-metallic materials, such polymers, collagen, proteins, drugs, and biologic materials, bioactive agents, therapeutic compounds, or combinations of these materials. If made of a non-radiopaque material, it should advantageously be doped or impregnated or chemically modified to be visible with one or more imaging techniques. Alternatively, it can be made of a material that is highly visible by means of MRI or ultrasound. The inner element 11 can be formed in various configurations, including, but not limited to, coils, rods, tubes, cables, braids, cut tubes, or other elongate, flexible forms. As shown, it is in the form of a helical coil, which may be preferred. In one specific embodiment, it is formed at least in part of a multi-filar coil configuration, as described in the co-owned and co-pending U.S. application Ser. No. 10/189,934; filed Jul. 2, 2002, the disclosure of which is incorporated herein by reference.

The intermediate element 12 may be formed as a coating, wrapping, tubular sleeve, or other construction to create a substantially continuous surface coaxially around the inner element 11. Alternatively, it can be formed into a cylinder and then skewered onto the inner core element 11, as described in the co-owned and co-pending U.S. application Ser. No. 10/157,621; filed May 29, 2002, the disclosure of which is incorporated herein by reference. The intermediate element 12 preferably covers all of the length of the inner element 11, except for short proximal and distal sections.

The intermediate element 12 may be made of any of various suitable, substantially non-metallic, biocompatible materials, including polymers, biopolymers, biologic materials, and combinations of these materials. Suitable polymers include cellulose, polypropylene, polyvinylpyrrolidone, polyacrylics, polylactides, polyamides, polyvinyl alcohol, polyester, polyurethane, polyglycolic acid, polyfluorocarbons, hydrogels, and silicones. Exemplary biologic materials include alginates, hyaluronic acid, fibrin, collagen and silk. Optionally, the intermediate element 12 can be impregnated, grafted, bound, or modified to deliver therapeutic compounds, proteins, genes, bioactive agents, or cellular material. See, e.g., U.S. Pat. No. 5,658,308 and International Publications Nos. WO 99/65401 and WO 00/27445, the disclosures of which are incorporated herein by reference. In one preferred embodiment, the intermediate element 12 is made of a state-of-the-art bioabsorbable or biodegradable polymer, such as, for example, those described in US Published Applications Nos. 2002/0040239 and 2002/0020417, the disclosures of which are incorporated herein by reference. In another preferred embodiment, the intermediate element 12 is made of a soft conformal material, and more preferably of an expansile material such as a hydrogel.

The most preferred material is an environmentally responsive hydrogel, such as that described in co-owned and co-pending U.S. application Ser. No. 09/804,935, the disclosure of which is incorporated herein by reference. Specifically, the hydrogels described in application Ser. No. 09/804,935 are of a type that undergoes controlled volumetric expansion in response to changes in such environmental parameters as pH or temperature. These hydrogels are prepared by forming a liquid mixture that contains (a) at least one monomer and/or polymer, at least a portion of which is sensitive to changes in an environmental parameter; (b) a cross-linking agent; and (c) a polymerization initiator. If desired, a porosigen (e.g., NaCl, ice crystals, or sucrose) may be added to the mixture, and then removed from the resultant solid hydrogel to provide a hydrogel with sufficient porosity to permit cellular ingrowth. The controlled rate of expansion is provided through the incorporation of ethylenically unsaturated monomers with ionizable functional groups (e.g., amines, carboxylic acids). For example, if acrylic acid is incorporated into the crosslinked network, the hydrogel is incubated in a low pH solution to protonate the carboxylic acids. After the excess low pH solution is rinsed away and the hydrogel dried, the hydrogel can be introduced through a microcatheter filled with saline at physiological pH or with blood. The hydrogel cannot expand until the carboxylic acid groups deprotonate. Conversely, if an amine-containing monomer is incorporated into the crosslinked network, the hydrogel is incubated in a high pH solution to deprotonate amines. After the excess high pH solution is rinsed away and the hydrogel dried, the hydrogel can be introduced through a microcatheter filled with saline at physiological pH or with blood. The hydrogel cannot expand until the amine groups protonate.

More specifically, in a preferred formulation of the hydrogel, the monomer solution is comprised of ethylenically unsaturated monomers, an ethylenically unsaturated crosslinking agent, a porosigen, and a solvent. At least a portion, preferably 10%-50%, and more preferably 10%-30%, of the monomers selected must be pH sensitive. The preferred pH sensitive monomer is acrylic acid. Methacrylic acid and derivatives of both acids will also impart pH sensitivity. Since the mechanical properties of hydrogels prepared exclusively with these acids are poor, a monomer to provide additional mechanical properties should be selected. A preferred monomer for providing mechanical properties is acrylamide, which may be used in combination with one or more of the above-mentioned pH sensitive monomers to impart additional compressive strength or other mechanical properties. Preferred concentrations of the monomers in the solvent range from 20% w/w to 30% w/w.

The crosslinking agent can be any multifunctional ethylenically unsaturated compound, preferably N, N'-methylenebisacrylamide. If biodegradation of the hydrogel material is desired, a biodegradable crosslinking agent should be selected. The concentrations of the crosslinking agent in the solvent should be less than about 1% w/w, and preferably less than about 0.1% w/w.

The porosity of the hydrogel material is provided by a supersaturated suspension of a porosigen in the monomer solution. A porosigen that is not soluble in the monomer solution, but is soluble in the washing solution can also be used. Sodium chloride is the preferred porosigen, but potassium chloride, ice, sucrose, and sodium bicarbonate can also be used. It is preferred to control the particle size of the porosigen to less than about 25 microns, more preferably less than about 10 microns. The small particle size aids in the suspension of the porosigen in the solvent. Preferred concentrations of the porosigen range from about 5% w/w to about 50% w/w, more preferably about 10% w/w to about 20% w/w, in the monomer solution. Alternatively, the porosigen can be omitted and a non-porous hydrogel can be fabricated.

The solvent, if necessary, is selected based on the solubilities of the monomers, crosslinking agent, and porosigen. If a liquid monomer (e.g. 2-hydroxyethyl methacrylate) is used, a solvent is not necessary. A preferred solvent is water, but ethyl alcohol can also be used. Preferred concentrations of the solvent range from about 20% w/w to about 80% w/w, more preferably about 50% w/w to about 80% w/w.

The crosslink density substantially affects the mechanical properties of these hydrogel materials. The crosslink density (and hence the mechanical properties) can best be manipulated through changes in the monomer concentration, crosslinking agent concentration, and solvent concentration. The crosslinking of the monomer can be achieved through reduction-oxidation, radiation, and heat. Radiation crosslinking of the monomer solution can be achieved with ultraviolet light and visible light with suitable initiators or ionizing radiation (e.g. electron beam or gamma ray) without initiators. A preferred type of crosslinking initiator is one that acts via reduction-oxidation. Specific examples of such red/ox initiators that may be used in this embodiment of the invention are ammonium persulfate and N,N,N',N'-tetramethylethylenediamine.

After the polymerization is complete, the hydrogen is washed with water, alcohol or other suitable washing solution(s) to remove the porosigen(s), any unreacted, residual monomer(s) and any unincorporated oligomers. Preferably this is accomplished by initially washing the hydrogel in distilled water.

As discussed above, the control of the expansion rate of the hydrogel is achieved through the protonation/deprotonation of ionizable functional groups present on the hydrogel network. Once the hydrogel has been prepared and the excess monomer and porosigen have been washed away, the steps to control the rate of expansion can be performed.

In embodiments where pH sensitive monomers with carboxylic acid groups have been incorporated into the hydrogel network, the hydrogel is incubated in a low pH solution. The free protons in the solution protonate the carboxylic acid groups on the hydrogel network. The duration and temperature of the incubation and the pH of the solution influence the amount of control on the expansion rate. Generally, the duration and temperature of the incubation are directly proportional to the amount of expansion control, while the solution pH is inversely proportional. It has been determined that the water content of the treating solution also affects the expansion control. In this regard, the hydrogel is able to expand more in the treating solution and it is presumed that an increased number of carboxylic acid groups are available for protonation. An optimization of water content and pH is required for maximum control on the expansion rate. After the incubation is concluded, the excess treating solution is washed away and the hydrogel material is dried. The hydrogel treated with the low pH solution has been observed to dry down to a smaller dimension than the untreated hydrogel. This is a desired effect since delivery of these hydrogel materials through a microcatheter is desired.

If pH sensitive monomers with amine groups were incorporated into the hydrogel network, the hydrogel is incubated in high pH solution. Deprotonation occurs on the amine groups of the hydrogel network at high pH. The duration and temperature of the incubation, and the pH of the solution, influence the amount of control on the expansion rate. Generally, the duration, temperature, and solution pH of the incubation are directly proportional to the amount of expansion control. After the incubation is concluded, the excess treating solution is washed away and the hydrogel material is dried.

For the embodiment of the vaso-occlusive device having an intermediate element formed of an expansile polymeric hydrogel, when the intermediate element 12 expands, the areas of the soft, conformal intermediate element 12 that are not covered or constrained by the outer element 13 extend radially outward through the openings or gaps, or between the coils of the outer element 13 (as described below) to form an undulating outer surface comprising a chain of arcuate segments, as a result of the constraint imposed by the outer element 13. Because the arcuate segments of the undulating outer surface contact the interior wall surface of a microcatheter through which the device is deployed only at or near tangential contact points proximate the apex of each segment, this undulating or arcuate configuration provides reduced friction as compared to a continuous or smooth surface of the same material.

The outer element 13 is a flexible, elongate, substantially tubular member, at least a substantial portion of the length of which, and preferably most of the length of which, includes or defines at least one opening or gap to allow the exposure and/or protrusion of the intermediate element 12. Suitable configurations for the outer element 13 include helical coils, braids, and slotted or spiral-cut tubes. The outer element 13 may be made of any suitable biocompatible metal or polymer, including those listed above for the inner element 11. For those embodiments using a soft, conformal intermediate element 12, the outer element 13 should have sufficient radial strength to compress or restrain the intermediate element 12.

In the most preferred embodiment, the device comprises an inner core element 11 formed of a tightly-wound ("close-wound") helical coil of a biocompatible metal wire (e.g., platinum alloy), an intermediate element 12 of a hydrophilic expansile polymer (e.g., hydrogel), and an outer element 13 in the form of a biocompatible metal or polymer helical coil that is open-wound for most of its length, with a close-wound proximal end section 14 and a close-wound distal end section 15. The open-wound portion of the outer element defines a single, continuous, helical opening or gap. A coupling element 16 is advantageously attached to the proximal end of the inner element 11 for detachable attachment to a deployment device (not shown). A rounded distal obturator tip 17 may be attached to the distal end of the inner element 11.

Figure 3:
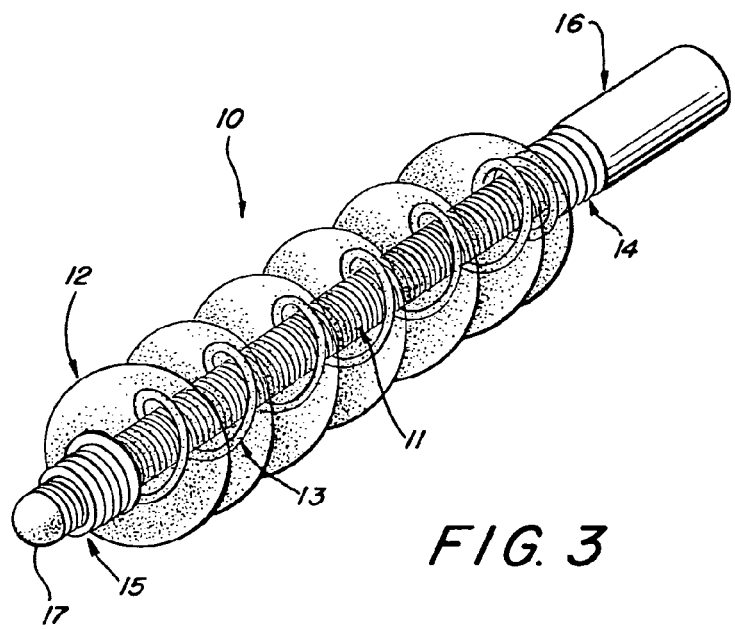
FIG. 3 is a perspective view, similar to that of FIG. 1, showing the expansile polymeric intermediate element in its expanded state.
Figure 4:
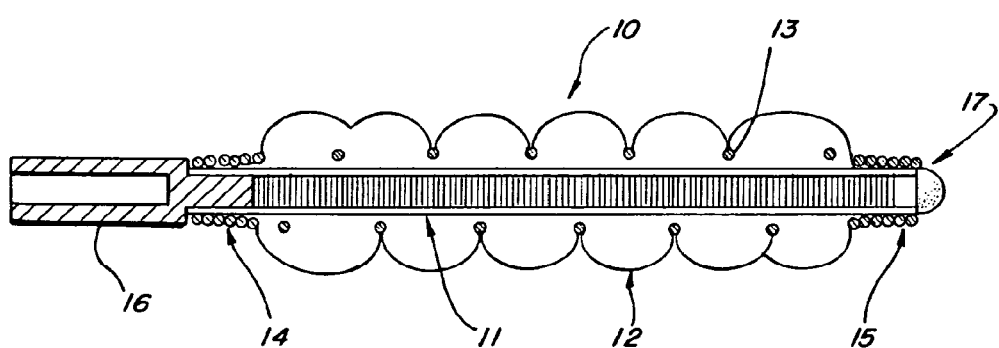
FIG. 4 is an axial cross-sectional view of FIG. 3.

In the above-described most preferred embodiment, the hydrogel of the intermediate element 12 expands or swells upon exposure to an aqueous environment (e.g., blood). Preferably, the hydrogel expands to between about two times and about 20 times its original volume. As shown in FIGS. 3 and 4, the swollen or expanded intermediate element 12 protrudes through the helical opening or gap defined between the coils of the open-wound section of the outer element 13 to form an undulating, convexly-curved surface defining a chain of arcuate or rounded segments, each having a diameter that is substantially greater than the diameter of the outer element 13. The open-wound section of the coil forming the outer element 13 preferably has a coil pitch that is at least one-half the diameter of the outer element 13. The coil is preferably made from a wire that has a diameter of no more than about 0.15 mm.

The helical outer element 13 described above may be considered as defining a single, helical opening or gap, or it may be viewed as defining a plurality of connected openings or gaps, each defined between an adjacent pair of windings of the coil of the outer element 13. Alternatively, if the outer element 13 is formed as a slotted tube, for example, the outer element 13 will be seen to define a plurality of discrete openings or gaps in its axial middle section that are functionally equivalent to the helical opening(s) defined in the illustrated embodiment. The device 10 can be constructed with various radial thickness of each coaxial element to provide different handling characteristics. Preferably, the inner element 11 has a diameter of between about 0.075 mm and 0.75 mm; the intermediate element 12 has a thickness of between about 0.025 mm and 1.00 mm; and the outer element 13 has a thickness of between about 0.025 mm and 0.25 mm. For the embodiments that use an expansile intermediate element 12, these thicknesses are measured in the non-expanded state. Preferably, the outer diameter of the outer element 13 is actually somewhat less than the expanded or swollen diameter of the intermediate element 12, so that the latter will readily expand through the openings or gaps in the outer element 13.

Figure 5:
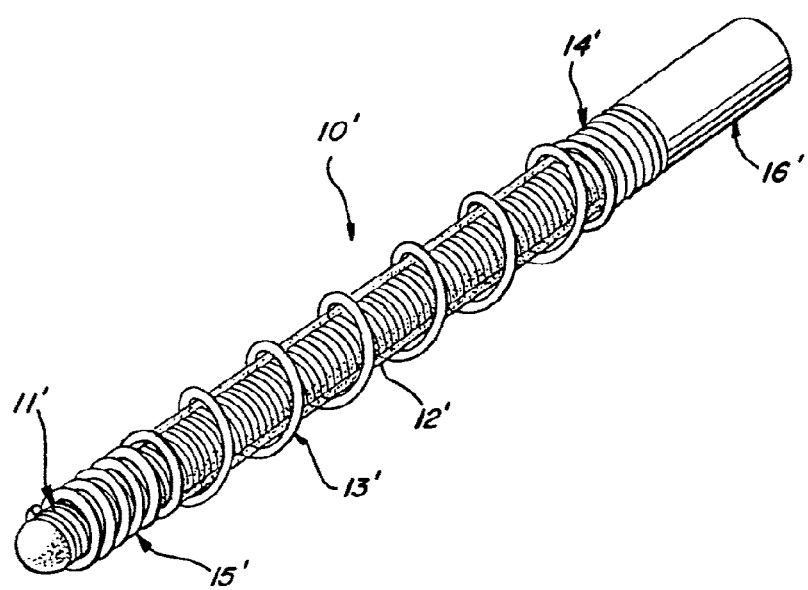
FIG. 5 is a perspective view of an alternative embodiment of the invention.

FIG. 5 shows a vaso-occlusive device 10' in accordance with an alternative embodiment of the invention. This embodiment includes an outer element 13' with a distal section 15' that is not close wound, but is, instead, made with small gaps of approximately 5% to 100% of the diameter of the wire or filament of which the outer element 13' is made. These gaps make the distal section 15' of the device 10' more flexible in the area where the outer element 13' overlaps the inner element 11'.

In the embodiment shown in FIG. 5, the proximal ends of both the inner element 11' and the outer element 13' are both advantageously attached to a coupling element 16' by soldering or welding. The attachment of both the inner element 11' and the outer element 13' to the coupling element 16' makes the proximal end of the device 10' more resistant to deformation during deployment and implantation.

As indicated above, the present invention provides good trackability in a microcatheter. In other words, it is easily advanced through a catheter without binding against or moving the catheter. This advantage is achieved through reduced friction and reduced buckling at the ends of the device. The force required to advance the device through a typical microcatheter would normally be less than about 0.7 lbs.

The device is preferably detachable from a flexible, elongate delivery apparatus (not shown), such as a wire, a pusher tube, or the like. Exemplary detachment systems known in the art include electrolytic, mechanical, electromechanical, thermal, ultrasonic, and hydraulic detachment mechanisms. The device may be formed into a secondary configuration, such as a helical coil, a sphere, an ovoid, or any other suitable two- or three-dimensional shape known in the art of vaso-occlusive devices. Alternatively, the device can be left in a relatively straight configuration with or without a curvature at the end such as a "J" configuration).

The device is useful for the occlusion and/or embolization of blood vessels, other vascular spaces such as aneurysms, and other tubular or saccular organs or spaces throughout the body. Specific applications where it may be useful include the occlusion of cerebral aneurysms, aortic aneurysms, fistulas, fallopian tubes, cardiac septal defects, patent foramen ovale, and the left atrial appendage of the heart. For some of these applications, it may be preferable to use devices with dimensions larger than those specified above.

Although preferred embodiments of the invention have been described in this specification and the accompanying drawings, it will be appreciated that a number of variations and modifications may suggest themselves to those skilled in the pertinent arts. Thus, the scope of the present invention is not limited to the specific embodiments and examples described herein, but should be deemed to encompass alternative embodiments and equivalents, as determined by a fair reading of the claims that follow.

The invention claimed is:

1. A method of occluding a body cavity, comprising:
    delivering an implant to a vascular abnormality of a body cavity with a delivery device, said implant comprising an open-coiled element surrounding a hydrogel element and defining a gap;

expanding said hydrogel element through said gap within said vascular abnormality at a controlled rate in response to an environmental parameter; and, detaching said implant from said delivery device.

2. The method of claim 1, wherein said hydrogel element surrounds a microcoil.

3. The method of claim 1, further comprising detaching a coupling element from a proximal end of said implant.

4. The method of claim 1, wherein said environmental parameter is temperature.

5. The method of claim 1, wherein said environmental parameter is pH.

6. The method of claim 1, wherein said expanding said hydrogel element at a controlled rate in response to an environmental parameter further comprises expanding said hydrogel element through gaps of said open-coiled element to form an exterior surface having an undulating configuration defining a chain of convexly-curved arcuate segments.

7. The method of claim 1, wherein said open-coiled element comprises a wire forming a helical configuration.

8. The method of claim 1, wherein said hydrogel element expands volumetrically.

9. A method of occluding a body cavity, comprising:
providing an implant; said implant having a first flexible hydrogel element coaxially located within a second flexible element;
delivering said implant with a delivery device to a vascular abnormality;
exposing said first flexible hydrogel element to fluid through gaps defined by said second flexible element;
detaching said implant from said delivery device; and,
allowing said first flexible hydrogel element to expand at a controlled rate within said second element responsive to an environmental parameter of said fluid.

10. The method of claim 9, further comprising a microcoil located within said first flexible hydrogel element and made of a biocompatible material selected from a group consisting of metal wire and polymeric filament.

11. The method of claim 9, further comprising expanding said first flexible hydrogel element through said gaps defined by said second flexible member.

12. The method of claim 9, wherein said second flexible element comprises an open-wound, helically-coiled wire.

13. The method of claim 9, wherein said first flexible hydrogel element has a rate of expansion responsive to a change in temperature or pH.

14. The method of claim 9, further comprising uncoupling a proximal end of said implant.

15. A vaso-occlusive device implantable in a vascular abnormality, comprising:
an expansile first hydrogel member expandable at a controlled rate in response to an environmental parameter;
a second member helically surrounding said first hydrogel member and defining a gap through which the first hydrogel member is exposed; and,
wherein said vaso-occlusive device is selectively detachable from a delivery device within a patient.

16. The vaso-occlusive device of claim 15, wherein said environmental parameter is pH.

17. The vaso-occlusive device of claim 15, wherein said environmental parameter is temperature.

18. The vaso-occlusive device of claim 15, wherein said second member is an open-wound helical coil defining said gap.

19. The vaso-occlusive device of claim 15, further comprising a third member located within said expansile first hydrogel member, and wherein said third member is a microcoil.

20. A vaso-occlusive device implantable in a vascular abnormality, comprising:
an open-coiled element;
an expansile hydrogel element exposed between loops of said open-coiled element and expandable at a controlled rate against said open-coiled element; and,
wherein said vaso-occlusive device is selectively detachable from a delivery device within a patient.

21. The vaso-occlusive device of claim 20, wherein said expansile hydrogel element volumetrically expands at a controlled rate in response to an environmental parameter.

22. The vaso-occlusive device of claim 21, wherein said environmental parameter is pH or temperature.

* * * * *